US007988966B2

United States Patent
Pavone et al.

(10) Patent No.: US 7,988,966 B2
(45) Date of Patent: Aug. 2, 2011

(54) METHOD FOR THE POTENTIATION OF OPIOID ANALGESICS EFFECTS ON PAIN

(75) Inventors: Flaminia Pavone, Rome (IT); Sara Marinelli, Rome (IT); Antonino Cattaneo, Rome (IT); Gabriele Ugolini, Rome (IT)

(73) Assignee: Lay Line Genomics S.p.A., Rome (IT)

( * ) Notice: Subject to any disclaimer, the term of this patent is extended or adjusted under 35 U.S.C. 154(b) by 0 days.

(21) Appl. No.: 11/921,266

(22) PCT Filed: Jun. 23, 2006

(86) PCT No.: PCT/IT2006/000488
§ 371 (c)(1),
(2), (4) Date: Jul. 30, 2008

(87) PCT Pub. No.: WO2006/137106
PCT Pub. Date: Dec. 28, 2006

(65) Prior Publication Data
US 2009/0123464 A1 May 14, 2009

(30) Foreign Application Priority Data

Jun. 24, 2005 (IT) .............................. RM2005A0332

(51) Int. Cl.
*A61K 39/395* (2006.01)
*C07K 16/28* (2006.01)
(52) U.S. Cl. ................ 424/143.1; 424/130.1; 424/141.1; 424/133.1; 530/387.1; 530/387.3; 530/388.22
(58) Field of Classification Search ........................ None
See application file for complete search history.

(56) References Cited

U.S. PATENT DOCUMENTS

2004/0131615 A1 * 7/2004 Shelton et al. ............. 424/145.1

FOREIGN PATENT DOCUMENTS

| WO | WO-97/21732 A | 6/1997 |
| WO | WO-00/73344 A2 | 12/2000 |
| WO | WO-2004/073653 A2 | 9/2004 |
| WO | WO-2004/096122 A | 11/2004 |
| WO | WO-2005/061540 A | 7/2005 |

* cited by examiner

*Primary Examiner* — Christine J Saoud
*Assistant Examiner* — Jon M Lockard
(74) *Attorney, Agent, or Firm* — Edwards Angell Palmer & Dodge LLP; Peter C. Lauro, Esq.; Melissa Hunter-Ensor, Esq.

(57) ABSTRACT

According to the invention there is provided use of an anti-TrkA antibody capable of inhibiting the binding between NGF and TrkA combined with at least one opioid analgesic for the preparation of a medicament for treating and/or preventing pain.

21 Claims, 7 Drawing Sheets

SEQUENCE LISTING

<160> NUMBER OF SEQ ID NOS: 6

<210> SEQ ID NO 1
<211> LENGTH: 106
<212> TYPE: PRT
<213> ORGANISM: Mus sp.

<400> SEQUENCE: 1

Asp Ile Val Leu Thr Gln Ser Pro Ala Ile Met Ser Ala Ser Leu Gly
 1               5                  10                  15

Glu Glu Val Thr Leu Thr Cys Ser Ala Ser Ser Val Ser Tyr Met
            20                  25                  30

His Trp Tyr Gln Gln Lys Ser Gly Thr Ser Pro Lys Leu Leu Ile Tyr
        35                  40                  45

Thr Thr Ser Asn Leu Ala Ser Gly Val Pro Ser Arg Phe Ser Gly Ser
    50                  55                  60

Gly Ser Gly Thr Phe Tyr Ser Leu Thr Ile Ser Ser Val Glu Ala Glu

```
            65                  70                  75                  80
Asp Ala Ala Asp Tyr Tyr Cys His Gln Trp Ser Ser Tyr Pro Trp Thr
                    85                  90                  95

Phe Gly Gly Gly Thr Lys Leu Glu Ile Lys
                100                 105

<210> SEQ ID NO 2
<211> LENGTH: 123
<212> TYPE: PRT
<213> ORGANISM: Mus sp.

<400> SEQUENCE: 2

Glu Val Lys Leu Val Glu Ser Gly Gly Gly Leu Val Gln Pro Gly Gly
  1               5                  10                  15

Ser Leu Lys Leu Ser Cys Ala Ala Ser Gly Phe Thr Phe Ser Thr Tyr
                 20                  25                  30

Thr Met Ser Trp Ala Arg Gln Thr Pro Glu Lys Arg Leu Glu Trp Val
             35                  40                  45

Ala Tyr Ile Ser Lys Gly Gly Ser Thr Tyr Tyr Pro Asp Thr Val
         50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Leu Tyr Tyr Cys
                 85                  90                  95

Ala Arg Gly Ala Met Phe Gly Asn Asp Phe Phe Pro Met Asp Arg
                100                 105                 110

Trp Gly Gln Gly Thr Ser Val Thr Val Ser Ser
            115                 120

<210> SEQ ID NO 3
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Asp Ile Val Leu Thr Gln Ser Pro Ser Leu Ser Ala Ser Val Gly
  1               5                  10                  15

Asp Arg Val Thr Ile Thr Cys Ser Ala Ser Ser Ser Val Ser Tyr Met
                 20                  25                  30

His Trp Tyr Gln Gln Lys Pro Gly Gln Ala Pro Lys Leu Leu Ile Tyr
             35                  40                  45

Thr Thr Ser Asn Leu Ala Ser Gly Val Pro Ser Arg Phe Ser Gly Ser
         50                  55                  60

Gly Ser Gly Thr Asp Tyr Thr Leu Thr Ile Ser Ser Leu Gln Pro Glu
 65                  70                  75                  80

Asp Val Ala Thr Tyr Tyr Cys His Gln Trp Ser Ser Tyr Pro Trp Thr
                 85                  90                  95

Phe Gly Gly Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160
```

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
        210

<210> SEQ ID NO 4
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Thr Tyr
            20                  25                  30

Thr Met Ser Trp Ala Arg Gln Ala Pro Gly Lys Gly Leu Glu Trp Val
        35                  40                  45

Ala Tyr Ile Ser Lys Gly Gly Gly Ser Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ser Ala Val Tyr Tyr Cys
                85                  90                  95

Ala Arg Gly Ala Met Phe Gly Asn Asp Phe Phe Pro Met Asp Arg
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

```
Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
    435                 440                 445

Leu Ser Pro Gly Lys
    450
```

<210> SEQ ID NO 5
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Thr Met Ser Trp Ala Arg Gln Ala Pro Gly Lys Gly Leu Glu Trp Val
        35                  40                  45

Ala Tyr Ile Ser Lys Gly Gly Gly Ser Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ser Ala Val Tyr Tyr Cys
            85                  90                  95

Ala Arg Gly Ala Met Phe Gly Asn Asp Phe Phe Pro Met Asp Arg
        100                 105                 110

Trp Gly Gln Gly Thr Leu Val Thr Val Ser Ser Ala Ser Thr Lys Gly
    115                 120                 125

Pro Ser Val Phe Pro Leu Ala Pro Ser Ser Lys Ser Thr Ser Gly Gly
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205
```

```
Asn His Lys Pro Ser Asn Thr Lys Val Asp Lys Arg Val Glu Pro Lys
    210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
            260                 265                 270
Ser His Glu Asp Pro Glu Val Lys Phe Asn Trp Tyr Val Asp Gly Val
        275                 280                 285
Glu Val His Asn Ala Lys Thr Lys Pro Arg Glu Glu Gln Tyr Ala Ser
    290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
            340                 345                 350
Gln Val Tyr Thr Leu Pro Pro Ser Arg Asp Glu Leu Thr Lys Asn Gln
        355                 360                 365
Val Ser Leu Thr Cys Leu Val Lys Gly Phe Tyr Pro Ser Asp Ile Ala
    370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
            420                 425                 430
Val Met His Glu Ala Leu His Asn His Tyr Thr Gln Lys Ser Leu Ser
        435                 440                 445
Leu Ser Pro Gly Lys
    450

<210> SEQ ID NO 6
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Thr Tyr
            20                  25                  30
Thr Met Ser Trp Ala Arg Gln Ala Pro Gly Lys Gly Leu Glu Trp Val
        35                  40                  45
Ala Tyr Ile Ser Lys Gly Gly Gly Ser Thr Tyr Tyr Pro Asp Thr Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Ser Ala Val Tyr Tyr Cys
                85                  90                  95
Ala Arg Gly Ala Met Phe Gly Asn Asp Phe Phe Pro Met Asp Arg
            100                 105                 110
```

```
Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
        210                 215                 220

Tyr Gly Pro Pro Cys Pro Ser Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
                260                 265                 270

Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
                420                 425                 430

Glu Ala Leu His Asn His Tyr Thr Gln Lys Ser Leu Ser Leu Ser Leu
            435                 440                 445

Gly Lys
    450
```

METHOD FOR THE POTENTIATION OF OPIOID ANALGESICS EFFECTS ON PAIN

Figure 1:
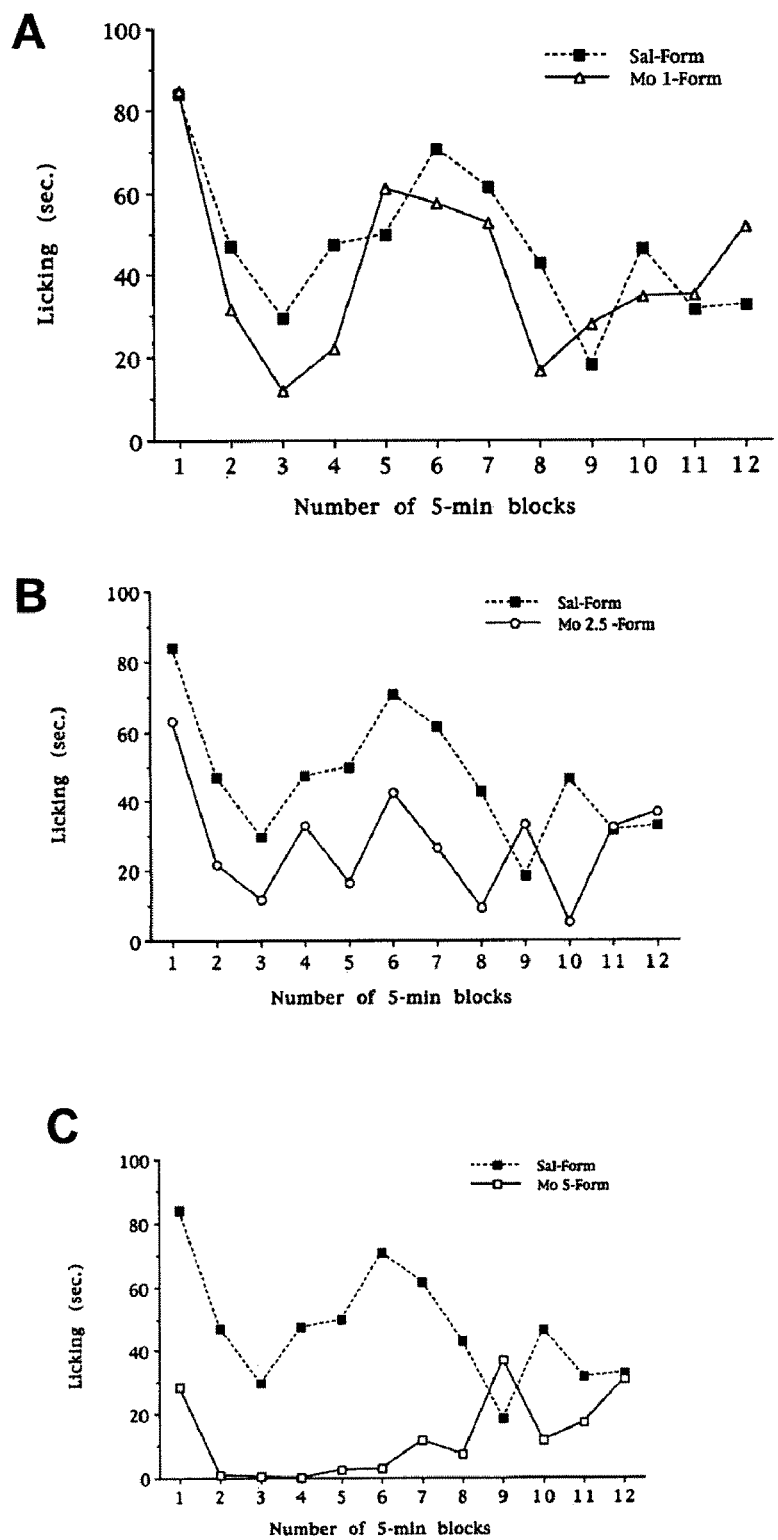

This application is the U.S. national phase application, pursuant to 35 U.S.C. §371, of PCT international application Ser. No. PCT/IT2006/000488, filed Jun. 23, 2006, designating the United States and published in English on Dec. 28, 2006 as publication WO 2006/137106 A2, which claims priority to Italian application Ser. No. RM2005A000332, filed Jun. 24, 2005. The entire contents of the aforementioned patent applications are incorporated herein by this reference.

BACKGROUND TO THE INVENTION

The present invention relates to molecules that are able to block TrkA activity for the potentiation of opioid analgesics effects on pain. In particular, the molecules are anti-TrkA antibodies showing a potentiation of the analgesic effect of opioids such as morphine.

STATE OF THE ART

The nociceptive signals afferent to the spinal cord are carried by the fibres Aδ and C, the cell bodies of which (primary sensitive neurons) are located in the spinal dorsal ganglia (DRG). The primary sensitive neurons release glutamate together with ATP as an excitatory neurotransmitter, and various other substances such as substance P and CGRP (calcitonin-gene-related-peptide), (Hunt and Mantyh, 2001). The release of these excitatory neurotransmitters is controlled by various classes of receptors present on the afferent terminals including those sensitive to capsaicin (vanilloid receptors, VR1), those activated by GABA, those activated by ATP itself and those activated by cannabinoids (CB1) (Sivilotti and Nistri, 1991; Hunt and Mantyh, 2001; Khakh, 2001; Morisset et al., 2001). One of the physiopathological whereby chronic pain occurs is allodynia, i.e. the transformation of stimuli that are not normally painful into painful sensations. This phenomenon involves various ionic currents and therefore different channels of the "ligand-gated" type, including the receptor for the capsaicin, VR1, and the ionotropic receptors for ATP (Khakh, 2001). The simultaneous activation of the receptors for VR1 and of those for ATP on spinal nociceptive interneurons generates a considerable accumulation of the excitatory synaptic signals with reinforcement of the painful stimulus transmission (Nakatsuka et al., 2002). From these observations it is therefore clear that the ATP receptors (especially those belonging to the P2X3 class) play a fundamental role in the pain pathways (Burnstock, 2001). These receptors are present on the peripheral nerve terminals activated by algogenic stimuli, on the cell bodies of the neurons in the DRGs and on the presynaptic terminals thereof, as well as on postsynaptic terminals in the spinal cord (Khakh, 2001). There is considerable evidence showing an involvement of the nerve growth factor (NGF) and its high-affinity receptor TrkA (Levi-Montalcini, 1987; Levi-Montalcini et al., 1996; Frade and Barde, 1998; Kaplan, 1998) in the molecular processes underlying the main kinds of "persistent" pain, indicating a major therapeutic area (that of pain, with particular reference to the "tonic" forms), for the antibodies which block the NGF/TrkA system (Levine, 1998). The development of sensitive nociceptive neurons depends greatly on NGF, and the responses of the adult nociceptors are modulated by the same factor (Julius and Basbaum, 2001). In particular, NGF exerts acute sensitisation to the capsaicin algogenic stimulus (Shu and Mendell, 1999). From a functional standpoint, nociceptive neurons, following chronic inflammation, develop alterations in the frequency and duration of their action potential. These phenomena regress by blocking endogenous NGF, leading to a significant attenuation of the hyperexcitability typical of states of chronic pain (Djouhri et al., 2001). NGF action in defining the pain threshold in adult nociceptors is mediated by the TrkA receptor, also through modulation of the response mediated by the VR1 receptor present on the nociceptive terminals. The TrkA dependent potentiation of the VR1 response is thought to occur through the intracellular transduction pathway of the phospholipase C gamma (PLCgamma, Chuang et al., 2001). This rapid TrkA mediated potentiation of nociceptor signalling and function could have an algogenic effect in acute and chronic pain settings. The peripheral NGF levels are increased in inflammatory processes, while the administration of exogenous NGF has a hyperalgesic effect on rats and produces muscular pain in humans. Furthermore, NGF produces hypersensitisation to heat stimulation in humans and mammals in general. NGF is released by mast cells, fibroblasts and other cell types in the peripheral sites where inflammatory processes occur. In particular, mast cells appear to play a fundamental role (Woolf et al., 1996). As they produce NGF and at the same time express functional TrkA receptors on their surface (Nilsson et al., 1997), they are able to respond to NGF itself, in the presence of lysophosphatidylserine (Horigome et al., 1993; Kawamoto et al., 2002). As a result, the NGF/TrkA system appears to mediate mastocyte activation through an autocrine positive feedback mechanism which allows local amplification of the algogenic inflammatory signal.

High levels of NGF are also found in neurons, where this neurotrophin is apparently responsible for the modifications of the nerve fibres, associated with pain (Harpf et al., 2002). In certain forms of cancer, the excess of NGF facilitates the growth and infiltration of nerve fibres with induction of oncological pain (Zhu et al., 1999). Recent experimental studies demonstrate how, by blocking NGF, it is possible to significantly reduce the formation of neuromas, responsible for neuropathic pain, without damaging the cell bodies of the lesioned neurons (Kryger et al., 2001). These results generated significant interest in therapeutic approaches based on the reduction of NGF effects for the treatment of acute and persistent pain (Saragovi and Gehring, 2000). In recent years, the involvement of the NGF/TrkA system in the molecular processes of pain transduction was also genetically demonstrated. In particular, mutations of the TrkA gene (localised on the chromosome 1q21-q22) are responsible for a hereditary recessive autosomic syndrome known as CIPA ("congenital insensitivity to pain with anhydrosis"), characterised by recurrent episodic fever, anhydrosis, absence of reaction to nociceptive stimuli, mental retardation and a tendency to self-mutilation (Indo et al., 1996; Saragovi and Gehring, 2000; Indo, 2001; Indo et al., 2001). Further confirmation of the involvement of NGF in the nociceptive response was recently obtained by the inventors with the characterisation of anti-NGF transgenic mice phenotype (AD11). In these animals, the ectopic expression of the anti-NGF antibody αD11 produces a functional block of NGF in adult age. Such block consistently translates into an increase in the latency time of the response to harmful heat stimuli (Capsoni et al., 2000; Ruberti et al., 2000). Numerous evidence indicates the system constituted by the nerve growth factor (NGF) and its high-affinity receptor TrkA as a possible target for pain therapy. For this reason, antibodies capable of neutralising the biological activity of the NGF/TrkA system by blocking the TrkA receptor may represent an important resource for pain therapy.

The authors of the present invention make use of antibodies (directed against the TrkA receptor) which are able to block the biological effects of NGF mediated by TrkA. The reagent MNAC13 is of particular interest.

The MNAC13 antibody is a mouse monoclonal antibody directed against the human TrkA receptor (Cattaneo et al., 1999; Pesavento et al., 2000), particularly in the inhibition of TrkA activation by NGF and the downstream biological functions, both in vitro and in vivo (Cattaneo et al., 1999; Pesavento et al., 2000). Anti-TrkA antibodies, including the MNAC13 antibody, having an antagonist activity preventing the functional activation of TrkA by NGF" are disclosed in EP 1.181.318. Derivatives of such antibody are also disclosed in WO2005/061540. However, the potentiation of the analgesic effect of opioids by such molecules is not disclosed.

The antibodies were characterised in detail from the point of view of the structure (Covaceuszach et al., 2001) and as for the molecular interaction with the TrkA receptor (Covaceuszach et al., 2005). On the basis of such in-depth structural knowledge, by means of an innovative method a humanised version of MNAC13 was generated (Hu-MNAC13), with the same antigen binding features as the parental antibody (patent application WO2005/061540).

The action of the MNAC13 antibody, as well as of the humanized MNAC13 antibody version (huMNAC13), was investigated in a classical model of persistent inflammatory pain, i.e. the mouse formalin test (Porro and Cavazzuti, 1993). When animals undergo this test, two behavioral phases can be distinguished, in terms of pain response. The two phases are separated by an interval of a few minutes during which the response to the painful stimulus is mild or absent. Phase 1 is determined by direct stimulation of nociceptive terminals (by formalin), whilst phase 2 is due to the subsequent inflammation. The action of the MNAC13 antibodies was compared to that of morphine, a traditional strong analgesic belonging to the opioid class, largely used to treat mild to severe pain (Przewlocki and Przewlocka, 2001), and the anti-NGF antibody αD11$_{[v1]}$. Opioid analgesics include all active principles, natural or synthetic, whose action is similar to that of morphine. Synthetic or semi-synthetic principles are derivatives of five chemical classes (phenanthrenes, phenylethylamine, phenylpiperidines, morphinans, and benzomorphinans). From the pharmacological point of view, they have different activities: they may be strong opioid receptor agonists (like morphine), moderate or weak agonists of the same receptors (like codeine), compounds with mixed antagonist/agonist activity (like nalbuphine), or partial agonists (like nalorphine). Of all these compounds, morphine remains the most largely used. However, despite its therapeutic properties, it has several side effects (sedative effect, nausea, vomiting, etc.). Moreover, morphine and the compounds belonging to this analgesic class show a fundamental disadvantageous characteristic that is the development of tolerance and physical addiction. There is therefore an urgent need to develop treatments using doses of this class of analgesics as low as possible, reducing the incidence of side effects and the probability to develop tolerance and or/addiction. For this purpose potentiation of the analgesic effect of opioids was investigated, with antibodies blocking the NGF/TrkA system.

The patent application WO2004/096122 describes a method for the treatment or the prevention of pain including the administration of an NGF antagonist and an opioid analgesic. The application refers, in particular, to an anti-NGF antibody and not to an antagonist of its receptor, TrkA.

SUMMARY OF THE INVENTION

The authors of the present invention have found that small amounts (below their efficacy threshold) of molecules able to block TrkA biological activity can potentiate the analgesic effect of opioids. Such combined therapy allows using a reduced opioid amount to obtain the same level of pain relief that would be achieved with a higher opioid dose if administered alone.

The object of the present invention is the use of an anti-TrkA antibody that is able to inhibit the binding between NGF and TrkA combined with at least one opioid analgesic for the preparation of a medicament for the treatment and/or the prevention of pain. Suitably the antibody blocks the biological activity of TrkA i.e. is an antagonistic antibody.

A molecule that blocks the biological activity of TrkA refers to a molecule that acts as an antagonist in terms of the NGF binding to the TrkA receptor, and which can be defined as a synthetic molecule or a monoclonal antibody or a biological/synthetic derivative thereof which:

i) binds to TrkA; and ii) inhibits the binding of NGF to the "native" TrkA receptor expressed on the surface of living cells; and iii) blocks the biological activity deriving from NGF binding to the same TrkA receptor.

The term "blocking the biological activity" does not simply mean blocking activation of the receptor, defined as blocking the conversion process of the receptor itself into an "active" state, but also the functional neutralisation of biological consequences downstream of the activation process: second messengers, new gene expression, phenotypic and functional modifications both at cell and system level. The molecule of the invention is not only able to block TrkA in a classic in vitro test (test of neuritic growth in PC12 cells), but also in vivo (functional block of the cholinergic neurons of the basal forebrain and block of the nociception in a classic "hot plate" test).

As noted above, antagonistic TrkA antibodies are disclosed in EP 1181318 and in WO2005/061540.

In an aspect of the invention the variable region of the antibody light chain comprises at least one of the complementarity determining regions (CDRs) having the sequence selected from aa. 24 to aa. 33 of SEQ ID No.1; from aa. 49 to aa. 55 of SEQ ID No. 1; from aa. 88 to aa. 96 of SEQ ID No. 1, more preferably two of the above CDRs, most preferably three of the above CDRs. The variable region of the antibody light chain may, for example, comprise essentially the sequence of SEQ ID No.1.

```
                                              (SEQ ID No 1)
                    CDR L1
DIVLTQSPAIMSASLGEEVTLTCSASSSVSYMHWYQQKSGTSPKLLIY

CDR L2                              CDR L3
TTSNLASGVPSRFSGSGSGTFYSLTISSVEAEDAADYYCHQWSSYPWT

FGGGTKLEIK.
```

In an aspect of the invention the variable region of the antibody heavy chain comprises at least one of the complementarity determining regions (CDRs) having the sequence selected from aa. 26 to aa. 35 of SEQ ID No. 2; from aa. 50 to aa. 66 of SEQ ID No. 2; from aa. 99 to aa. 112 of SEQ ID No. 2, more preferably two of the above CDRs, most preferably three of the above CDRs. The variable region of the antibody light chain may, for example, comprise essentially the sequence of SEQ ID No.2.

(SEQ ID No 2)
CDR_H1
EVKLVESGGGLVQPGGSLKLSCAAS<u>GFTFSTYTMS</u>WARQTPEKRLEWVA

CDR_H2
<u>YISKGGGSTYYPDTVKG</u>RFTISRDNAKNTLYLQMSSLKSEDTALYYCAR

CDR_H3
<u>GAMFGNDFFFPMDR</u>WGQGTSVTVSS.

The antibody may be in single chain form and comprises a light chain variable region and a heavy chain variable region joined by a linker.

Alternatively the antibody may comprise two light chains and two heavy chains.

Alternatively the antibody may be a Fab (monovalent fragment antigen binding) fragment. Fab fragments may be prepared by recombinant means ab initio or may be prepared by enzymatic (e.g. papain)_proteolysis of a whole antibody.

Alternatively the antibody may be a Fab2 fragment. Fab2 fragments may be prepared by recombinant means ab initio or may be prepared by enzymatic (e.g. pepsin)_proteolysis of a whole antibody.

In a preferred aspect of the invention the anti-TrkA antibody is a human or humanised antibody. The skilled in the art shall select the proper humanisation method to design the antibody, a preferred method is the method as disclosed in WO 2005/061540. Exemplary humanised antibodies comprise a light chain variable region which is a humanised derivative of SEQ ID No 1 (a mouse origin sequence). Exemplary humanised antibodies comprise a heavy chain variable region which is a humanised derivative of SEQ ID No 2 (a mouse origin sequence).

In a preferred aspect of the invention the variable region of the humanised antibody light chain comprises essentially the sequence from aa. 1 to aa. 106 of SEQ ID No. 3. In a more preferred aspect the humanised antibody light chain has essentially the sequence of SEQ ID No. 3.

hMNAC13 Vk hCk
(SEQ ID No. 3)
*DIVLTQSPSSLSASVGDRVTITC<u>SASSSVSYMH</u>WYQQKPGQAPKLLIY*

*<u>TTSNLAS</u>GVPSRFSGSGSGTDYTLTISSLQPEDVATYYC<u>QWSSYPWT</u>*

*FGGGTKVEI*KRTVAAPSVFIFPPSDEQLKSGTASVVCLLNNFYPREAK

VQWKVDNALQSGNSQESVTEQDSKDSTYSLSSTLTLSKADYEKHKVYA

CEVTHQGLSSPVTKSFNRGEC.

In a preferred aspect of the invention the variable region of the humanised antibody heavy chain comprises essentially the sequence from aa. 1 to aa. 123 of SEQ ID No. 4.

In a more preferred aspect the humanised antibody heavy chain has essentially a sequence selected from SEQ ID No. 4, SEQ ID No. 5, SEQ ID No. 6.

hMNAC13 VH hIgG1
(SEQ ID No. 4)
*EVQLLESGGGLVQPGGSLRLSCAAS<u>GFTFSTYTMS</u>WARQAPGKG*

*LEWVA<u>YISKGGGSTYYPDTVKG</u>RFTISRDNSKNTLYLQMNSLRAEDSA*

*V*YYCAR<u>GAMFGNDFFFPMDR</u>WGQGT*L*VTVSSASTKGPSVFPLAPSSKST

SGGTAALGCLVKDYFPEPVTVSWNSGALTSGVHTFPAVLQSSGLYSLSSV

VTVPSSSLGTQTYICNVNHKPSNTKVDKRVEPKSCDKTHTCPPCPAPEL

LGGPSVFLFPPKPKDTLMISRTPEVTCVVVDVSHEDPEVKFNWYVDGV

EVHNAKTKPREEQYNSTYRVVSVLTVLHQDWLNGKEYKCKVSNKALPA

PIEKTISKAKGQPREPQVYTLPPSRDELTKNQVSLTCLVKGFYPSDIA

VEWESNGQPENNYKTTPPVLDSDGSFFLYSKLTVDKSRWQQGNVFSCS

VMHEALHNHYTQKSLSLSPGK.

hMNAC13 VH hIgG1 (N297A)
(SEQ ID No. 5)
*EVQLLESGGGLVQPGGSLRLSCAAS<u>GFTFSTYTMS</u>WARQAPGKG*

*LEWVA<u>YISKGGCSTYYPDTVKG</u>RFTISRDNSKNTLYLQMNSLRAEDSA*

*V*YYCAR<u>GAMFGNDFFFPMDR</u>WGQGT*L*VTVSSASTKGPSVFPLAPSSKST

SGGTAALGCLVKDYFPEPVTVSWNSGALTSGVHTFPAVLQSSGLYSLSS

VVTVPSSSLGTQTYICNVNHKPSNTKVDKRVEPKSCDKTHTCPPCPAPE

LLGGPSVFLFPPKPKDTLMISRTPEVTCVVVDVSHEDPEVKFNWYVDGV

EVHNAKTKPREEQYASTYRVVSVLTVLHQDWLNGKEYKCKVSNIKALP

APIEKTISKAKGQPREPQVYTLPPSRDELTKNQVSLTCLVKGFYPSDI

AVEWESNGQPENNYKTTPPVLDSDGSFFLYSKLTVDKSRWQQGNVFSC

SVMHEALHNHYTQKSLSLSPGK.

hMNAC13 VH hIgG4
(SEQ ID No. 6)
*EVQLLESGGGLVQPGGSLRLSCAAS<u>GFTFSTYTMS</u>WARQAPGKG*

*LEWVA<u>YISKGGCSTYYPDTVKG</u>RFTISRDNSKNTLYLQMNSLRAEDSA*

*V*YYCAR<u>GAMFGNDFFFPMDR</u>WGQGT*L*VTVSSTKGPSVFPLAPCSRSTSE

STAALGCLVKDYFPEPVTVSWNSGALTSGVHTFPAVLQSSGLYSLSSVV

TVPSSSLGTKTYTCNVDHKPSNTKVDKRVESKYGPPCPSCPAPEFLGGP

SVFLFPPKPKDTLMISRTPEVTCVVVDVSQEDPEVQFNWYVDGVEVHNA

KTKPREEQFNSTYRVVSVLTVLHQDWLNGKEYKCKVSNKGLPSSIEKT

ISKAKGQPREPQVYTLPPSQEEMTKNQVSLTCLVKGFYPSDIAVEWES

NGQPENNYKTTPPVLDSDGSFFLYSRLTVDKSRWQEGNVFSCSVMHEA

LHNHYTQKSLSLSLGK.

Italics: variable regions, Bold: mutations in the mouse sequence in the humanization process, Underlined: CDRs.

A still further object of the present invention is the use of an anti-TrkA antibody that is able to inhibit the binding between NGF and TrkA combined with at least one opioid analgesic to prepare a remedy for treatment of pain of any etiology, including but not limited to acute and chronic pain, any pain with an inflammatory component, and any pain in which an opioid analgesic is usually prescribed. More preferably the pain is caused by pancreatitis, kidney stones, headaches, dysmenorrhoea, musculoskeletal pain, sprains, visceral pain, ovarian cysts, prostatitis, cystitis, interstitial cystitis, inflammatory bowel disease post-operative pain (including dental pain), post-surgical pain, migraine, trigeminal neuralgia, pain from burns and/or wounds, pain associated with trauma (including traumatic head injury), neuropathic pain, post-herpetic neuralgia, pain associated with musculoskeletal diseases, rheumatoid arthritis, osteoarthritis, ankylosing spondylitis, periarticular pathologies, oncological pain (including "breakthrough pain" and pain associated with terminal cancer), pain from bone metastases, pain from HIV, pain from myocardial infarction.

According to International Association for the Study of Pain (IASP, www.iasp-pain.org <http://www.iasp-pain.org/>), pain is generally defined as "An unpleasant sensory and emotional experience associated with actual or potential tissue damage, or described in terms of such damage or both". The essential element in all forms of pain is the activation of specialized high-threshold receptors and nerve fibers to warn the organism of potential tissue damage. The involvement of inflammatory cells and processes is a common element in many pain states. The term "acute pain" means immediate, generally high threshold, pain brought about by injury such as a cut, crush, burn, or by chemical stimulation. The term "chronic pain," as used herein, means pain other than acute pain. It is understood that chronic pain often is of relatively long duration, for example, months or years and can be continuous or intermittent.

In one particular embodiment of the invention the pain to be treated is a persistent form of pain, e.g. oncological, neuropathic or rheumatic pain.

The anti-TrkA antibody of the invention is suitably administered systemically. Systemic administration can be performed by injection, e.g. continuous intravenous infusion, bolus intravenous infusion, subcutaneous or intramuscular injection. Alternatively other forms of administration (e.g. oral, mucosal, via inhalation, sublingually, etc.) may also be used. Local delivery of the antibody can be performed by local administration e.g. intra-articular injection or subcutaneous, intramuscular injection in the affected tissue area.

The anti-TrkA antibody will suitably be formulated in a pharmaceutical composition appropriate for the intended route of administration. Solutions for injection will suitably contain the antibody dissolved or dispersed in an aqueous medium (e.g. water for injection) as appropriate containing appropriate buffers and molarity modifiers e.g. phosphate, salt and/or dextrose.

Treatment regimen i.e. dose, timing and repetition, can be represented by single or repeated administrations (e.g. injections) of the product by the chosen administration route. The interval of dose administration can be subject to modifications depending on the extent and duration of the clinical response, as well as the particular individual and the individual clinical history.

Combined administration includes both simultaneous administration and/or administration at different times. The TrkA antagonist and the opioid analgesic may be administered with different frequencies and doses, i.e. a TrkA antibody may be administered 1 to 3 times a week or maybe 1 to 3 times a month in single doses in the 0.01-500 mg/kg range (e.g. 0.1-50 mg/kg), whilst the opioid analgesic may be administered with greater frequency, with a lower or equal dose to that normally used for this category of analgesics. For example a suitable dose of morphine (as morphine hydrochloride) would be in the 0.05-5 mg/kg range. For example a suitable dose of fentanyl (as fentanyl citrate) would be in the 0.0005-0.05 range. TrkA antibody and the opioid analgesic may be administered in different ways and the doses may vary during the administration according to patient's response to the treatment. Adequate administration pathways possible (for one and/or the other component of the combination) are the following: oral, intravenous, sublingual, subcutaneous, intraarterial, intramuscular, rectal, intraspinal, intrathorax, intraperitoneal, intraventricular, transdermic, by inhalation. The administration pathway may be systemic (as in the case of intravenous administration) or localized. A preventive administration, before the onset of pain, may also be considered.

Suitably the anti-TrkA antibody has a long duration of action. In particular the clinical effect of the antibody extends following administration may be as long as 21 days as determined from animal studies. Furthermore preliminary data implies that anti-TrkA antibodies may manifest clinical benefit for a longer period than that in which its presence can be detected in a relevant biological matrix such as serum or plasma following its administration.

In a preferred aspect, the opioid analgesic is a compound or a combination of one or more compounds selected from the following list: morphine, codeine, dihydrocodeine, diacetylmorphine, hydrocodone, hydomorphone, levorphanol, oxymorphone, alfentanil, buprenorphine, butorphanol, fentanyl, sufentanyl, meperidine, methadone, nabulfina, propoxyphene, pentazocine; and their pharmaceutically acceptable salt derivatives, In one embodiment the opioid analgesic is morphine or a pharmaceutically acceptable salt thereof. In another embodiment the opioid analgesic is fentanyl or a pharmaceutically acceptable salt thereof.

Suitably the quantity of anti-TrkA antibody is such that the opioid dose is reduced by at least 5% e.g. at least 20% for example at least 50% of that necessary to produce the same analgesic effect by itself.

Suitably the quantity of opioid analgesic is such that the TrkA antibody dose is reduced by at least 5% e.g. at least 20% for example at least 50% of that necessary to produce the same analgesic effect by itself.

Another object of the invention is a pharmaceutical formulation comprising in pharmaceutically acceptable and effective doses, at least one anti-TrkA antibody and at least one analgesic opioid. Preferably, the formulation is contained in a single pharmaceutical composition. More preferably, the formulation is constituted by two pharmaceutical compositions, the first one comprising the molecule able to block the biological activity of TrkA receptor, and the second one including the analgesic opioid.

A further object of the invention is an anti-TrkA antibody of the invention for use in combination with an analgesic opioid for the treatment of pain.

Another object is a method of treatment and/or prevention of pain in a subject comprising administering to the subject an effective amount of an anti-TrkA antibody and an effective amount of an analgesic opioid to treat and/or prevent pain in said subject.

There is also provided a kit comprising a composition containing an anti-TrkA antibody and an analgesic opioid together with instructions directing administration of said composition to a subject in need of treatment and/or prevention of pain thereby to treat and/or prevent pain in said subject.

This invention will now be described providing non limiting examples thereof with particular reference to the following figures:

FIG. 1: Effect of morpine (A) 1 mg/kg, (B) 2.5 mg/kg, (C) 5 mg/kg on mouse formalin test (n=10 for each experimental group). Morphine was injected intraperitoneally 15 minutes prior to starting the test and the total "Licking" time (response to pain) was measured in seconds. Saline solution (Sal) was injected to negative controls. Time intervals of 5 minutes were considered. Each time interval was analyzed by means of one factor variance analysis test (ANOVA). The first 8 intervals (=total time 40 min) correspond to the duration of the test. The animals were also observed during the 20 minutes immediately after the test. (A) 1 mg/kg of morphine is completely ineffective; (B) 2.5 mg/kg of morphine have a significant analgesic effect; (C) 5 mg/kg of morphine block the response to formalin consistently.

Figure 2:
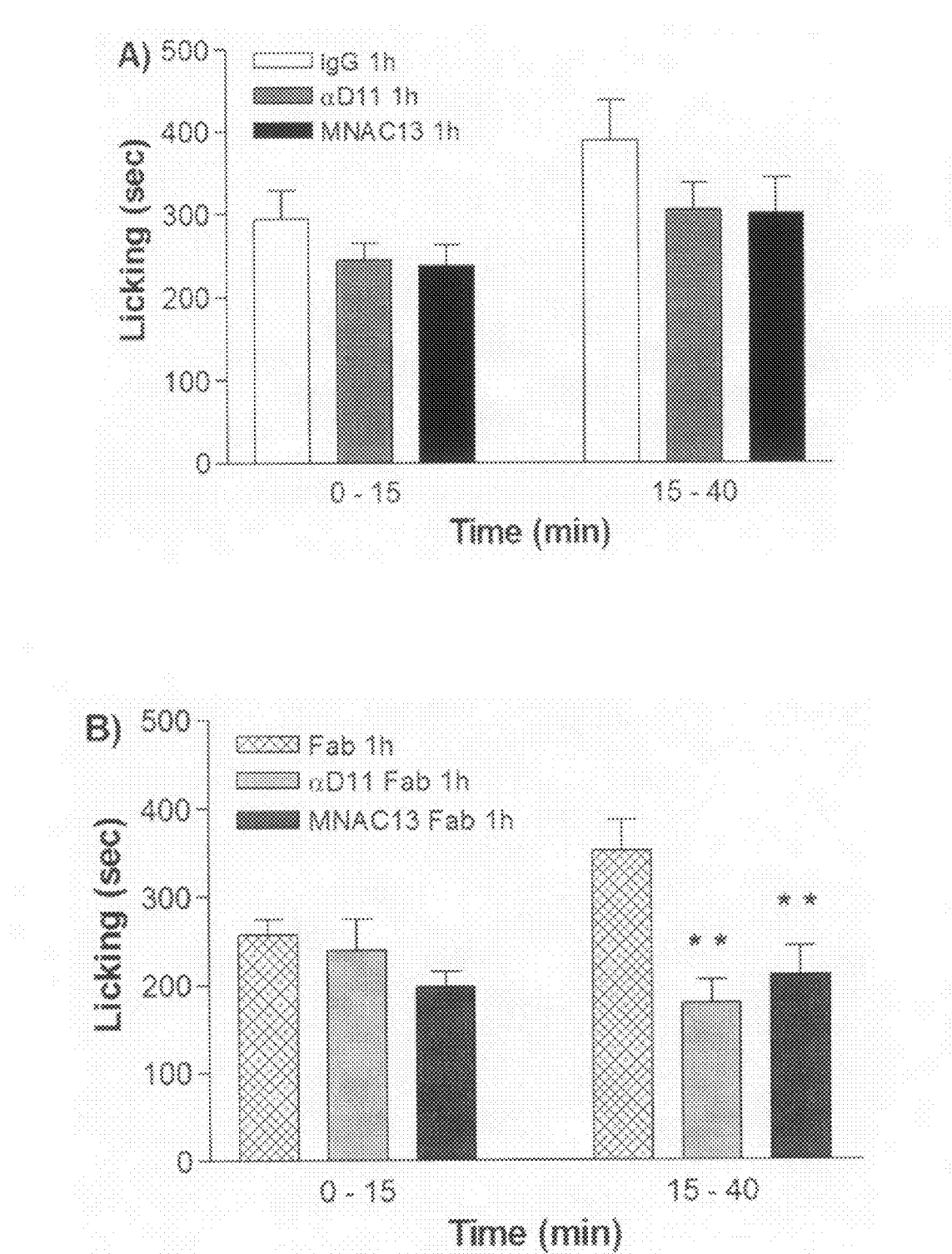

FIG. 2: Formalin test in mouse: Effect of the anti-NGF αD11 and anti-TrkA MNAC13 monoclonal antibodies on the pain response (Licking) when antibodies were injected 1 hour prior to the test, as indicated in the method section. (A) anti-NGF αD11 monoclonal antibody (Mab format: 12.5 μg/20 μl) and anti-TrkA MNAC13 monoclonal antibody (Mab format: 60 μg/20 μl); (B) Fab (monovalent fragment antigen binding) of the αD11 antibody (12.5 μg/20 μl) and Fab of the MNAC13 antibody (60 μg/20 μl). Irrelevant mouse immunoglobulins (IgG, 60 μg/20 μl) and murine irrelevant Fab (Fab, 60 μg/20 μl) were used as controls. The total licking time is divided into phase 1 (early phase=0-15 min) and phase 2 (late phase=15-40 min).

Experimental groups: (A) IgG (n=11), αD11 (n=10), MNAC13 (n=10); (B) Fab (n=9), αD11 Fab (n=10), MNAC13 Fab (n=10). **$p<0.01$ vs. control group (Fisher's PLSD Test). Fabs of the 2 antibodies show analgesic properties (limited to phase 2).

Figure 3:
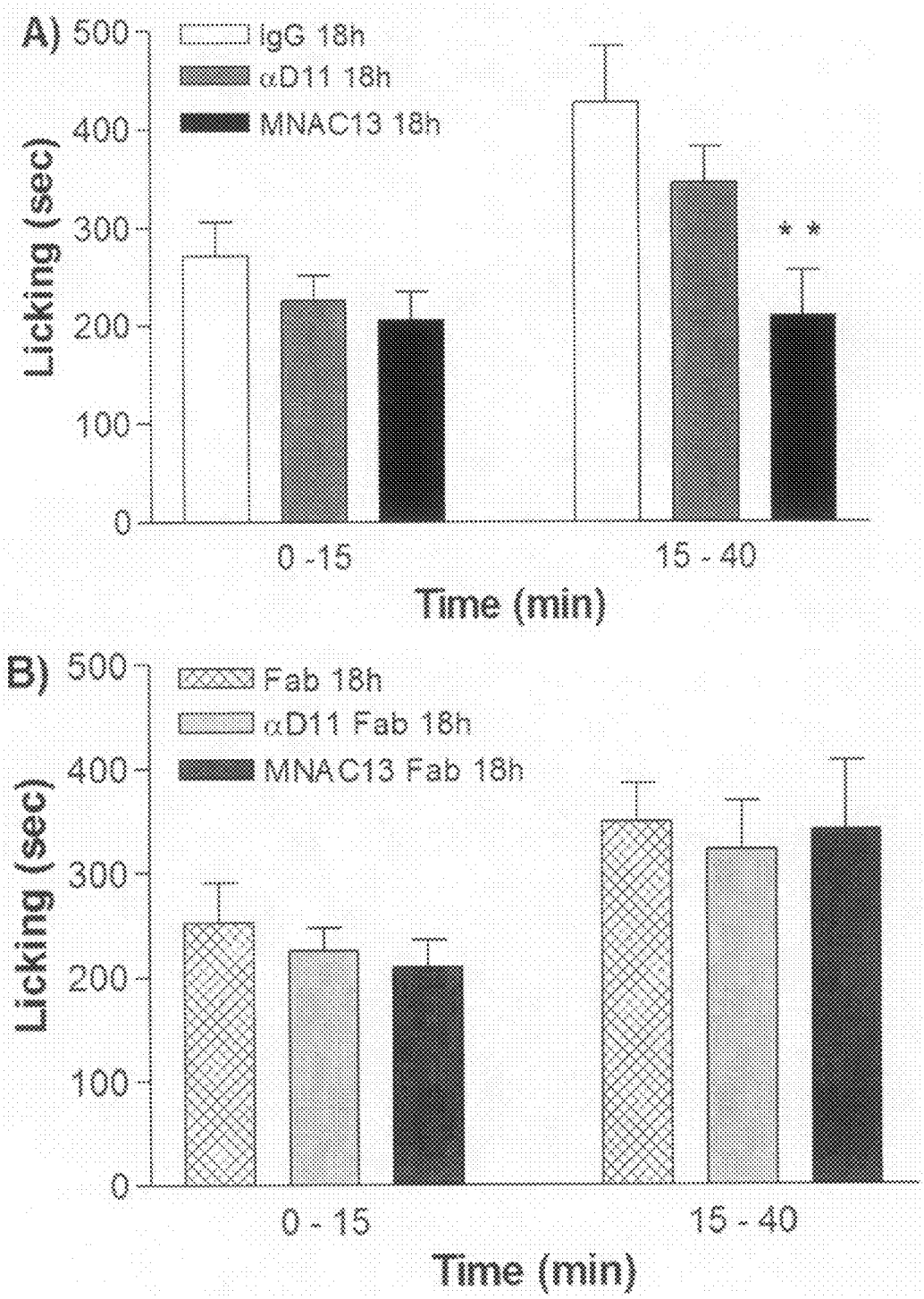

FIG. 3: Formalin test in mouse: Effect of the anti-NGF αD11 and anti-TrkA MNAC13 monoclonal antibodies on pain response (Licking) when the antibodies were injected 18 hours prior to the test, as indicated in the method section. (A) anti-NGF αD11 monoclonal antibody (Mab format: 12.5 μg in a total injection volume of 20 μl) and anti-TrkA MNAC13 monoclonal antibody (format Mab: 60 μg, in a total injection volume of 20 μl); (B) Fab (monovalent fragment antigen binding) of the αD11 antibody (12.5 μg in a total injection volume of 20 μl) and Fab of the MNAC13 antibody (60 μg, in a total injection volume of 20 μl). Irrelevant mouse immunoglobulins (IgG, 60 μg, in a total injection volume of /20 μl) and irrelevant murine Fab (Fab, 60 μg in a total injection volume/20 μl) were used as control. The total licking time is divided into phase 1 (early phase=0-15 min) and phase 2 (late phase=15-40 min).

Experimental groups: (A) IgG (n=10), αD11 (n=8), MNAC13 (n=9); (B) Fab (n=10), αD11 Fab (n=8), MNAC13 Fab (n=8). **$p<0.01$, vs. control group (Fisher's PLSD Test). MNAC13 (Mab) produces a significant analgesic effect (limited to phase 2).

Figure 4:
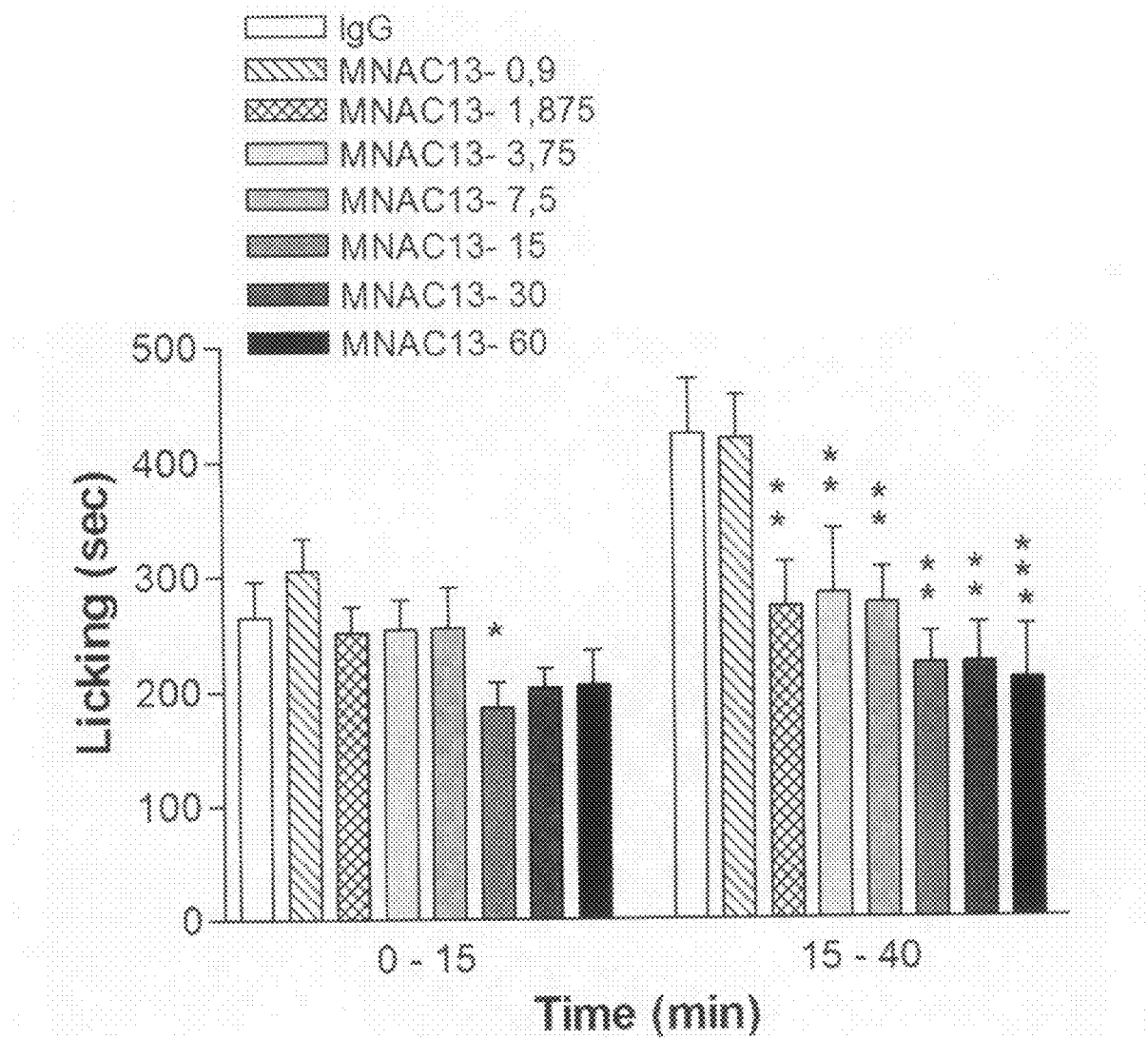

FIG. 4: Dose-response study of the anti-TrkA MNAC13 antibody in the formalin test (mouse), both for the early phase (phase 1=0-15 min), and for the late one (phase 2=15-40 min). The antibody was administered, 18 hours prior to the test as indicated in the method section. Experimental groups for single dose of MNAC13: 0.9 μg: n=8; 1.875 μg: n=10; 3.75 μg: n=10; 7.5 μg: n=10; 15 μg: n=10; 30 μg: n=10; 60 μg: n=9. Mouse Immunoglobulins (IgG, 60 μg n=12) were injected as control.

*$p<0.05$, $p<0.01$, *$p<0.001$ vs. control IgG group (Fisher's PLSD Test). Only the lowest dose (0.9 μg, equal to approximately 25 μg/kg) did not show any analgesic property. The intermediate dose of 15 μg (equal to approximately 0.4 mg/kg) is already able to produce the maximal effect observed (reduction by approximately 52% of the licking time in phase 2) and is the only dose displaying a statistically significant effect on phase 1 of the test.

Figure 5:
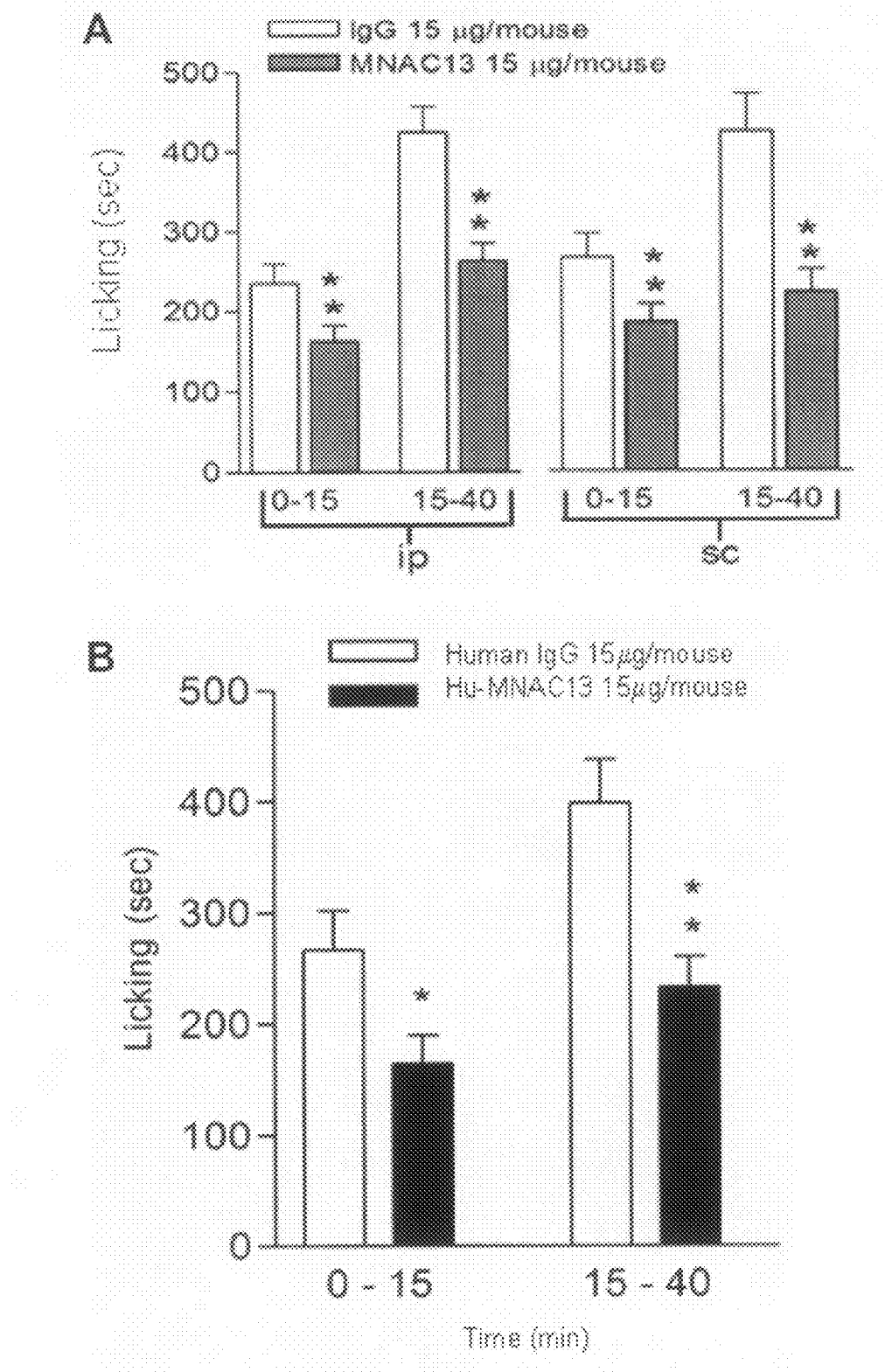

FIG. 5: Effect of anti-TrkA MNAC13 monoclonal antibody and its humanized counterpart (Hu-MNAC13) in the formalin test (mouse). (A) 15 μg of MNAC13 was given either sc (subcutaneously) or ip (intraperitoneally) to mice, 18 h before testing. Irrelevant mouse immunoglobulins (IgG) were used as controls. Experimental groups: IgG (ip, n=10); IgG (sc, n=9); MNAC13 (ip, n=9); MNAC13 (sc, n=8). Statistical analysis (two way ANOVA) of both early and late phase results showed a significant effect for treatment ($F_{13,66}$-P0.0008 for early phase; $F_{21,657}$-P<0.0001 for late phase), but no significance for the administration route and interaction (treatment*administration route). Post-hoc comparisons (Tukey/Kramer) revealed a significant difference (**$p<0.01$) between MNAC13 and IgG treatment groups for both early and late phase. MNAC13 induces analgesia in the formalin test, independently of the administration route. (B) A 15 μg dose of Hu-MNAC13 (IgG4) was given ip to mice, 18 h before testing. Irrelevant human immunoglobulins (IgG) were used as controls. Experimental groups: Human IgG (n=6); Hu-MNAC13 (n=9). T-Student test *$p<0.05$, **$p<0.005$. The results were comparable to those obtained with the mouse MNAC13 antobody (panel A).

Figure 6:
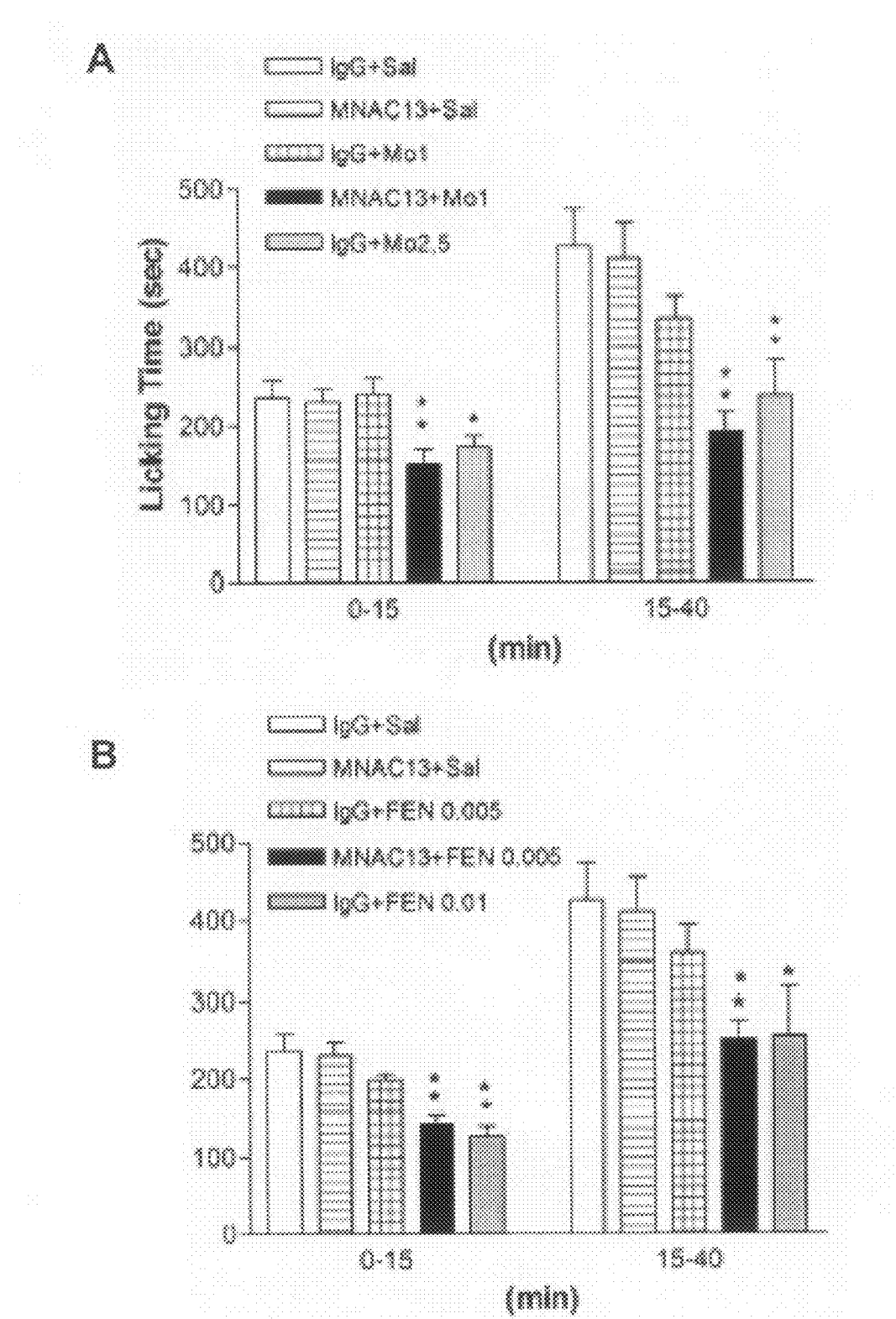

FIG. 6: Potentiation effect of MNAC13 (anti-TrkA) on opioid-induced analgesia (formalin test in mouse: A, morphine; B, fentanyl). Each mouse was randomly assigned to one of the different experimental groups and subcutaneously (sc) injected 18 hours before the test with anti-TrkA (mouse MNAC13, 0.9 μg per animal, approximately equivalent to 25 μg/kg, ineffective dose per se) antibody or irrelevant mouse IgGs (antibody dose: 25 μg/kg per animal) as indicated in the method section. (A) Morphine hydrochloride was injected i.p. 15 min before testing. (B) Fentanyl was injected sc 20 min before testing.

Experimental groups: Saline(Sal) and IgG (n=10); IgGs and morphine 1 mg/kg (Mo1) (n=9); IgGs and morphine 2.5 mg/kg (Mo2.5) (n=9); MNAC13 (mouse) and saline (n=11); MNAC13 (mouse) and morphine 1 mg/kg (Mo1) (n=11); IgGs and fentanyl 0.005 mg/kg (FEN 0.005) (n=8); IgGs and fentanyl 0.01 mg/kg (FEN 0.01) (n=7); MNAC13 and fentanyl (0.01 mg/kg (FEN 0.01) (n=8). One-way ANOVA followed by post-hoc comparisons (Tukey/Kramer). *$p<0.05$, **$p<0.005$ vs. control group.

Figure 7:
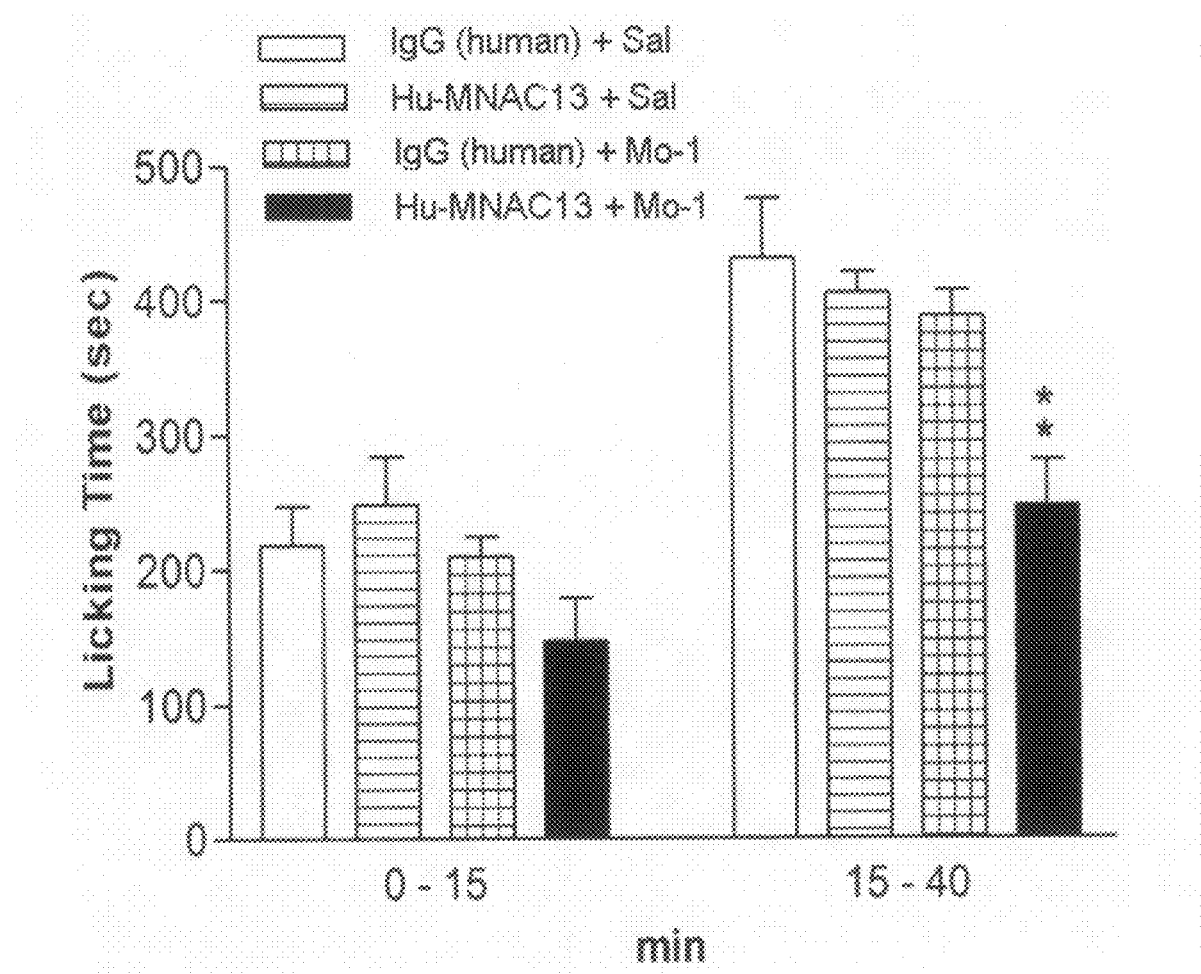

FIG. 7: Potentiation effect of humanized MNAC13 (Hu-MNAC13) on morphine-induced analgesia (formalin test in mouse).

Each mouse was randomly assigned to one of the different experimental groups and subcutaneously (sc) injected 18 hours before the test with anti-TrkA antibody (Hu-MNAC13; antibody dose: 25 μg/kg, per se ineffective) or irrelevant human IgGs (antibody dose: 25 μg/Kg), as indicated in the method section. Morphine hydrochloride (1 mg/kg=Mo-1, dose per se ineffective) was injected i.p. 15 min before testing. Morphine negative controls were injected with saline (Sal). Experimental groups: Sal and IgG (n=8); IgG and Mo-1 (n=6); Sal and Hu-MNAC13 (n=8); Hu-MNAC13 and Mo-1 (n=8). One-way ANOVA followed by post-hoc comparison (Tukey/Kramer): **$p<0.001$ vs. control group.

METHODS

Monoclonal Antibodies Production

The monoclonal antibodies MNAC13 and αD11 were produced from a hybridoma supernatant, according to standard methods, disclosed above (Galfre and Milstein, 1981; Cattaneo et al., 1988; Cattaneo et al., 1999). The supernatant containing each antibody was subjected to precipitation (29% ammonium sulphate), followed by dialysis against PBS 1X (Spectra-Por 12/14K membrane, Spectrum) and affinity chromatography on sepharose protein G column (4-Fast Flow, Amersham Biosciences). Elution was performed by means of a low pH (HCl 5 mM) solution that was neutralised upon collection. The final eluate was concentrated (Amicon Ultra-15, 50K, Millipore) to obtain preparations of purified antibody with concentrations between 1 and 5 mg/ml.

The Fab (Monovalent Fragment Antigen binding) version of the αD11 and MNAC13 antibodies were produced as previously described (patent application WO 05/061540, Covaceuszach et al., 2004).

Briefly, Fab fragments were obtained from the correspondent whole monoclonal antibodies (IgG format) by papain proteolysis, followed by a ion exchange chromatography purification step and concentration of the Fab fragments collected in the flow-through. In order to separate the Fab fragments from the quite low amount of uncleaved IgG that was still present, size exclusion chromatography on a Superdex G75 column (Pharmacia) was performed using an FPLC system (Pharmacia), followed by a final concentration step.

As far as the humanised versions of the 2 antibodies (Hu-αD11 and Hu-MNAC13) are concerned, they were also purified as disclosed above, starting from the supernatants of stably transfected cell lines, which were stable cotransfectants for the heavy chain (pVH/CMVexpress) and the light chain (pVL/CMVexpress) of each antibody. The vectors used were previously disclosed (patent application WO 05/061540). The stable co-transfected clones were obtained through double selection with G418 and mycophenolic acid. In order to produce the IgG4 variant of Hu-αD11, since the pVH/CMVexpress vector comprises the constant part of human IgG1, this was replaced by the corresponding Fc region of IgG4 (cloned by RT-PCR from human lymphocyte RNA). The IgG1*variant (=IgG1 with the N297A mutation described by Bolt et al., 1993) was generated by site directed mutagenesis.

Animals

Male CD1 mouse (Charles River Labs, Como, Italia) weighing approximately 35 g were used. On their arrival to the laboratory (at least 2 weeks before the experiment), they were housed in standard transparent plastic cages (4 per cage), at a constant temperature (22±1° C.) and relative humidity (60%), with a light/dark cycle rule (light 07:00-19:00) and with no water or food limitation. The experiments took place between 09:00 and 14:00. The animals were treated and handled in compliance with the IASP Ethical Committee ("International Association for the Study of Pain") guidelines and with the Italian national law (DL116/92, application of the European directive 86/609/EEC) on the use of animals for research purposes. All the necessary efforts were made to minimize animal suffering and to use the lowest possible number of animals, sufficient to produce reliable scientific data.

Formalin Test

The mice nociceptive response to formalin was tested. Each experimental group included 10 animals (unless stated otherwise). Mice were randomly assigned to experimental groups. 30 minutes prior to the test, the animal to be tested was placed in a transparent plastic cage (30×12×13 cm), where it was free to move in all directions. A mirror placed underneath the cage and a video camera placed opposite allowed a complete view of the hind legs during the observation period. Each mouse was treated with antibodies blocking NGF (αD11) or TrkA (MNAC13 or huMNAC13), e.g. with irrelevant antibodies (mouse IgG) or saline, through subcutaneous injection (s.c) in the dorsal part of the right hind paw, performed 1 to 18 hours prior to the injection (s.c) of formalin (5% in saline solution) in the same paw. A Hamilton micro syringe with a 26 diameter needle was used for the injections (injection volume equal to 20 µl). In some experiments, antibody (MNAC13 to Hu-MNAC13) injection was performed intraperitoneally (ip) 18 h before testing.

Morphine (morphine hydrochloride, Guieu) was injected intraperitoneally (i.p) at a final concentration between 1 mg/kg and 5 mg/kg (in saline solution), 15 min prior to the formalin test.

Fentanyl citrate (Hameln pharmaceuticals GmbH), doses employed: 0.01 or 0.005 mg/kg was administered subcutaneously (dorsal injection) to animals 20 min before testing. The choice of fentanyl doses to be tested was based on published protocols (Seguin et al., 1995; Meert and Vermeirsch, 2005).

The "Licking" activity, that is the total time spent by the animal licking and/or biting the injected paw, was recorded continuously for 40 minutes (divided into observation time intervals of 5 min). During each session of the test, as well as the "Licking", general activities and "self-grooming" activities (intended as grooming of the face) were also recorded. General activity is conventionally intended as the time the animal spends in horizontal locomotory activities and in exploring activities, including moments when the animal is in a vertical position or leans out.

With regards to the antibodies administration, the tested doses are summarized in the following table:

| Antibody | Format | Used doses (µg/20 µl) |
|---|---|---|
| MNAC13 | Whole monoclonal (Mab) | 60 µg; 30 µg; 15 µg; 7.5 µg; 3.75 µg; 1.875 µg; 0.9 µg |
| MNAC13 | Monovalent fragment (Fab) | 60 µg |
| MNAC13 | Humanized antibody (huMNAC13) in Mab format | 15 µg; 7.5 µg; 3.75 µg; 1.875 µg; 0.9 µg |
| αD11 | Whole monoclonal (Mab) | 12.5 µg |
| αD11 | Monovalent fragment (Fab) | 12.5 µg |
| Mouse IgG | Whole monoclonal (Mab) | 60 µg |
| Mouse IgG | Monovalent fragment (Fab) | 60 µg |

In some experiments, MNAC13 (15 µg, roughly equivalent to 0.4 mg/Kg), Hu-MNAC13 (15 µg, roughly equivalent to 0.4 mg/Kg) and mouse/human control Immunoglobulins (15 µg, roughly equivalent to 0.4 mg/Kg) were also given through the ip administration route.

Statistical Analysis

The formalin test was performed in a double-blinded manner. Formalin pain responses were separated into an early phase (from 0 to 15 min) and a late phase (from 15 to 40 min). The 2 phases were analyzed separately using one factor variance analysis test (ANOVA), except for experiments summarized in FIG. 5A, were a two way ANOVA (treatment and administration route factors) was performed. The same type of statistical analysis was performed on the general and "self-grooming" activities. When appropriate, "post-hoc" comparisons were drawn using either Fisher PLSD or Tukey/Kramer tests, as indicated. A simple Student T-test was employed to analyse results of FIG. 5B (effect of a single dose of Hu-MNAC13 vs human IgG, given ip).

RESULTS

Formalin produced the typical two-phase response, with a first phase of "Licking" activity, and a second phase of intense response to pain, starting 15 minutes after formalin injection. Subcutaneous administration of irrelevant mouse immunoglobulins (IgG) or of their monovalent version (Fab) had no effect on the response to pain. The response of the animals treated with IgG matched with that of the animals treated with Saline. In addition, general activity and "grooming" were indistinguishable amongst both the treated group and the control group, proving the specific feature of the pharmacological effect of the treatment.

Single Dose Studies

The first series of experiments evaluated the analgesic effect of 3 different doses of morphine (1 mg/kg; 2.5 mg/kg; 5 mg/kg) on the response to pain induced by formalin injection. The graphics (FIG. 1) relate to a period of observation of 60 minutes (divided into 5 min intervals), including the time of the actual test (first 40 minutes) and the following 20 minutes.

Considering the first 40 min, while the highest morphine dose was able to strongly reduce the pain response (FIG. 1C) and the intermediate dose substantially reduced by 50% the licking time (FIG. 1B), the lowest dose (1 mg/kg) proved to be totally ineffective, both in the first (0-15 min) and in the second phase (15-40 min, FIG. 1A).

When anti-NGF and anti-TrkA antibodies were used, the pain response (measured as "Licking" time), was differentially affected, depending on the format of the antibody (Whole immunoglobulin=Mab; monovalent fragment antigen binding=Fab).

In the first single dose study, the MNAC13 and αD11 antibodies were administered one hour prior to the test in Mab format (FIG. 2A) or in Fab format (FIG. 2B). The variance analysis did not highlight any significant analgesic effect for the antibodies in Mab format, both in the early phase ($F_{2,28}$: 1.217; p=0.3114), and the late phase ($F_{2,28}$: 1.393; p=0.2650). On the contrary, the administration of the antibodies in Fab format (αD11 Fab: 12.5 µg/20 µl; MNAC13 Fab: 60 µg/20 µl) revealed a significant reduction of the response to pain (analgesic effect) in the late phase of the test ($F_{2,26}$: 8.340 p<0.01), whilst no statistically significant changes were observed in the early phase ($F_{2,26}$: 1.608; p=0.2195).

When the antibodies were administered (same single doses), 18 hours prior to the formalin test (FIGS. 3A and 3B), the anti-NGF (αD11) and anti-TrkA (MNAC13) antibodies revealed an effect on the licking response that was different from that observed when administered 1 hour prior to the test. When compared to irrelevant mouse immunoglobulins (IgG), neither of the antibodies showed a significant effect on the early phase ($F_{2,24}$: 1.226; p=0.3112); however, as for the late phase, whilst MNAC13 produced a significant reduction in the response to pain ($F_{2,24}$: 5.129; p<0.01), the effect of αD11 was not statistically significant (FIG. 3A). This result showed the non-equivalence of the two molecular targets represented by the NGF ligand and the TrkA receptor. In a well known model of persistent inflammatory pain (formalin test), the functional block of the receptor (with MNAC13 blocking antibody) produced an analgesic effect, that was not detectable (at least with the same administration protocol), by blocking the ligand (with the αD11 blocking antibody). As shown on FIG. 3B, neither antibody, if administered 18 hours prior to the test in Fab format, was able to produce a significant analgesic effect both in the early phase ($F_{2,23}$: 0.468; p=0.6318) and in the late phase ($F_{2,23}$: 0.074; p=0.9293).

Dose-Response Study for MNAC13

A dose-response study (formalin test in mouse) was performed with the MNAC13 anti-TrkA antibody, based on the significant results obtained in the single dose studies (administration 18 hours prior to the test). The analysis of the response to pain ("Licking" time) showed (FIG. 4) a significant analgesic effect for all tested doses for the late phase of the test (F7,71: 4,134; p<0.001), with the exception of the lowest (0.9 µg/20 µl volume of injection, equal to approx. 25 µg/kg). It should be noted that three of the MNAC13 effective doses (1.875 µg; 3.75 µg; 7.5 µg) were smaller than the αD11 dose (12.5 µg) used in the single dose studies. This confirms a fundamental difference in analgesic efficacy between anti-NGF and anti-TrkA antibodies in the formalin test using this administration protocol.

MNAC13 doses higher than 15 µg (equal to approx. 0.4 mg/kg) did not show any increase in the average analgesic efficacy in the late phase of the test: The maximum effect of reduction of pain response (about 52% of the control) could be already obtained with 15 µg. This is also the only dose for which a small but statistically significant effect was observed in the early phase of the formalin test (FIG. 4).

FIG. 5A shows that the analgesic properties of the 15 µg dose are independent of the administration route. Indeed, the same effect on licking behaviour was observed when the antibody was injected s.c. or i.p.

When the Hu-MNAC13 was administered i.p. in the same kind of experiment at the dose of 15 µg, a similar analgesic effect, as compared to the corresponding dose of parental MNAC13, was observed (FIG. 5A).

Synergistic Effect of Anti-TrkA Antibody MNAC13 and Opioids

By employing the formalin test, it was also possible to show that MNAC13 (and its humanized counterpart) could act synergistically with opioids. Using the previously described administration protocol (18 hours prior to the test), animals were treated with an ineffective dose (25 µg/kg) of MNAC13 after an i.p ineffective dose (1 mg/kg) of morphine, or fentanyl (0.005 mg/kg). The results of the combined treatment (compared to all related cross check controls in which MNAC13 was replaced by irrelevant immunoglobulins, while opioids analgesics were replaced by saline solution) showed a surprising as well as significant potentiation effect (FIG. 6). The joint administration of ineffective doses of MNAC13 and morphine produced a significant reduction of pain response ("Licking time"), which was more evident in the late phase of the test.

As for the combined administration of morphine and MNAC13 (FIG. 6A), in phase 2, the licking time was reduced by 40% compared to the respective IgG+Sal control group. For both phases of the formalin test, the combined administration of two sub-threshold doses of MNAC13 (25 µg/kg) and morphine (1 mg/kg) produced an analgesic effect that was comparable to the (per se effective) 2.5 mg/kg dose of morphine.

Similar results were obtained when another opioid (fentanyl) was given in combination with MNAC13 (FIG. 6B), indicating that the potentiation of opioid-induced analgesia could be obtained independently of the opioid used. For both phases of the formalin test, the combined administration of two sub-threshold doses of MNAC13 (25 µg/kg) and fentanyl (0.005 mg/kg) produced an analgesic effect that was comparable to the (per se effective) 0.01 mg/kg dose of fentanyl (FIG. 6B).

Similar results were obtained when MNAC13 was replaced by its humanized variant (Hu-MNAC13) as shown in FIG. 7.

The potentiation of opioid-induced analgesia by antibodies blocking the TrkA receptor presents remarkable consequences from a therapeutic point of view. The joint administration of MNAC13 (or of its humanised version, as well as of any other derivative that maintains the blocking properties of the parental antibody) allows the use of lower doses of morphine (or other opioids), normally ineffective, consequently reducing the incidence of the side effects and the probability of developing drug tolerance or addiction.

BIBLIOGRAPHY

Berardi N, Cellerino A, Domenici L, Fagiolini M, Pizzorusso T, Cattaneo A, Maffei L (1994) Proc Natl Acad Sci USA 91:684-688.

Capsoni S, Ugolini G, Comparini A, Ruberti F, Berardi N, Cattaneo A (2000) Proc Natl Acad Sci USA 97:6826-6831.
Cattaneo A, Rapposelli B, Calissano P (1988) J Neurochem 50:1003-1010.
Cattanco A, Capsoni S, Margotti E, Righi M, Kontsekova E, Pavlik P, Filipcik P, Novak M (1999) J Neurosci 19:9687-9697.
Chuang H H, Prescott E D, Kong H, Shields S, Jordt S E, Basbaum A I, Chao M V, Julius D (2001) Nature 411:957-962.
Covaceuszach S, Cattaneo A, Lamba D (2001) Acta Crystallogr D Biol Crystallogr 57:1307-1309.
Covaceuszach S, Cattaneo A, Lamba D (2005) Proteins 58:717-727.
Covaceuszach S, Cassetta A, Cattaneo A, Lamba D (2004) Acta Crystallogr D Biol Crystallogr 60:1323-1327.
Djouhri L, Dawbarn D, Robertson A, Newton R, Lawson S N (2001) J Neurosci 21:8722-8733.
Frade J M, Barde Y A (1998) Bioessays 20:137-145.
Galfre G, Milstein C (1981) Methods Enzymol 73:3-46.
Harpf C, Dabernig J, Humpel C (2002) Muscle Nerve 25:612-615.
Hempstead B L (2002) Curr Opin Neurobiol 12:260-267.
Horigome K, Pryor J C, Bullock E D, Johnson E M, Jr. (1993) J Biol Chem 268:14881-14887.
Hunt S P, Mantyh P W (2001) Nat Rev Neurosci 2:83-91.
Indo Y (2001) Hum Mutat 18:462-471.
Indo Y, Tsuruta M, Hayashida Y, Karim M A, Ohta K, Kawano T, Mitsubuchi H, Tonoki H, Awaya Y, Matsuda I (1996) Nat Genet 13:485-488.
Indo Y, Mardy S, Miura Y, Moosa A, Ismail E A, Toscano E, Andria G, Pavone V, Brown D L, Brooks A, Endo F, Matsuda I (2001) Hum Mutat 18:308-318.
Julius D, Basbaum A I (2001) Nature 413:203-210.
Kaplan D R (1998) Prog Brain Res 117:35-46.
Kawamoto K, Aoki J, Tanaka A, Itakura A, Hosono H, Arai H, Kiso Y, Matsuda H (2002) J Immunol 168:6412-6419.
Khakh B S (2001) Nat Rev Neurosci 2:165-174.
Kryger G S, Kryger Z, Zhang F, Shelton D L, Lineaweaver W C, Buncke H J (2001) J Hand Surg [Am] 26:635-644.
Lee R, Kermani P, Teng K K, Hempstead B L (2001) Science 294:1945-1948.
Levi-Montalcini R (1987) Science 237:1154-1162.
Levi-Montalcini R, Skaper S D, Dal Toso R, Petrelli L, Leon A (1996) Trends Neurosci 19:514-520.
Levine J D (1998) Neuron 20:649-654.
Meert T F, Vermeirsch H A (2005) Pharmacol Biochem Behav 80:309-326.
Molnar M, Ruberti F, Cozzari C, Domenici L, Cattaneo A (1997) Neuroreport 8:575-579.
Molnar M, Tongiorgi E, Avignone E, Gonfloni S, Ruberti F, Domenici L, Cattaneo A (1998) Eur J Neurosci 10:3127-3140.
Morisset V, Ahluwalia J, Nagy I, Urban L (2001) Eur J Pharmacol 429:93-100.
Nakatsuka T, Furue H, Yoshimura M, Gu J G (2002) J Neurosci 22:1228-1237.
Nilsson G, Forsberg-Nilsson K, Xiang Z, Hallbook F, Nilsson K, Metcalfe D D (1997) Eur J Immunol 27:2295-2301.
Nykjaer A, Lee R, Teng K K, Jansen P, Madsen P, Nielsen M S, Jacobsen C, Kliemannel M, Schwarz E, Willnow T E, Hempstead B L, Petersen C M (2004) Nature 427:843-848.
Pesavento E, Margotti E, Righi M, Cattaneo A, Domenici L (2000) Neuron 25:165-175.
Porro C A, Cavazzuti M (1993) Prog Neurobiol 41:565-607.
Przewlocki R, Przewlocka B (2001) Eur J Pharmacol 429:79-91.
Ramer M S, Bradbury E J, McMahon S B (2001) J Neurochem 77:864-875.
Ruberti F, Capsoni S, Comparini A, Di Daniel E, Franzot J, Gonfloni S, Rossi G, Berardi N, Cattaneo A (2000) J Neurosci 20:2589-2601.
Saragovi H U, Gehring K (2000) Trends Pharmacol Sci 21:93-98.
Seguin L, Le Marouille-Girardon S, Millan M J (1995) Pain 61:325-343.
Sevcik M A, Ghilardi J R, Peters C M, Lindsay T H, Halvorson K G, Jonas B M, Kubota K, Kuskowski M A, Boustany L, Shelton D L, Mantyh P W (2005) Pain 115:128-141.
Shu X, Mendell L M (1999) Neurosci Lett 274:159-162.
Sivilotti L, Nistri A (1991) Prog Neurobiol 36:35-92.
Winston J, Toma H, Shenoy M, Pasricha P J (2001) Pain 89:181-186.
Woolf C J, Ma Q P, Allchome A, Poole S (1996) J Neurosci 16:2716-2723.
Zhu Z, Friess H, diMola F F, Zimmermann A, Graber H U, Korc M, Buchler M W (1999) J Clin Oncol 17:2419-2428.

The invention claimed is:

1. An analgesic pharmaceutical formulation comprising a therapeutically effective amount of at least one anti-TrkA antibody, wherein the antibody is capable of inhibiting the binding between NGF and TrkA, and at least one analgesic opioid and a pharmaceutically acceptable carrier, wherein the anti-TrkA antibody is a humanized antibody in which the variable region of the light chain comprises the sequence from amino acid 1 to amino acid 106 of SEQ ID NO. 3.

2. The formulation according to claim 1, wherein the formulation comprises a single pharmaceutical composition.

3. The formulation according to claim 1, wherein the formulation comprises two pharmaceutical compositions, the first one comprising the anti-TrkA antibody and the second one comprising the analgesic opioid.

4. The formulation according to claim 1, wherein the opioid analgesic is a compound or a combination of one or more compounds selected from the group consisting of morphine, codeine, diyhydrocodeine, diacetylmorphine, hydrocodone, hydomorphone, levorphanol, oxymorphone, alfentanil, buprenorphine, butorphanol, fentanyl, sufentanyl, meperidine, methadone, nabulfina, propoxyphene, pentazocine and their pharmaceutically acceptable salt derivatives.

5. The formulation according to claim 1, wherein the opioid analgesic is morphine or a pharmaceutically acceptable salt thereof.

6. The formulation according to claim 1, wherein the opioid analgesic is fentanyl or a pharmaceutically acceptable salt thereof.

7. A kit comprising a composition comprising at least one anti-TrkA antibody, wherein the antibody is a humanized antibody in which the variable region of the light chain comprises the sequence from amino acid 1 to amino acid 106 of SEQ ID NO. 3 and is capable of inhibiting the binding between NGF and TrkA, at least one analgesic opioid and instructions directing administration of said composition to a subject in need of treatment and/or prevention of pain.

8. The kit according to claim 7, wherein the opioid analgesic is a compound or a combination of one or more compounds selected from the group consisting of morphine, codeine, diyhydrocodeine, diacetylmorphine, hydrocodone, hydomorphone, levorphanol, oxymorphone, alfentanil, buprenorphine, butorphanol, fentanyl, sufentanyl, meperidine, methadone, nabulfina, propoxyphene, pentazocine and their pharmaceutically acceptable salt derivatives.

9. The kit according to claim 7, wherein the opioid analgesic is morphine or a pharmaceutically acceptable salt thereof.

10. The kit according to claim 7, wherein the opioid analgesic is fentanyl or a pharmaceutically acceptable salt thereof.

11. A method for treating and/or preventing pain in a subject in need thereof comprising administering to said patient a therapeutically effective amount of at least one anti-TrkA antibody, wherein the antibody is capable of inhibiting the binding between NGF and TrkA, and at least one analgesic opioid, and a pharmaceutically acceptable carrier, wherein the anti-TrkA antibody is a humanized antibody in which the variable region of the light chain comprises the sequence from amino acid 1 to amino acid 106 of SEQ ID NO. 3, thereby treating pain in said subject.

12. The method according to claim 11, wherein the antibody is capable of blocking the biological activity of TrkA.

13. The method according to claim 11, wherein the humanized antibody light chain has the sequence of SEQ ID NO: 3.

14. The method according to claim 11, wherein the humanized antibody heavy chain has a sequence selected from SEQ ID NO: 4, SEQ ID NO: 5, and SEQ ID NO: 6.

15. The method according to claim 11, wherein the opioid analgesic is a compound or a combination of one or more compounds selected from the group consisting of morphine, codeine, diyhydrocodeine, diacetylmorphine, hydrocodone, hydomorphone, levorphanol, oxymorphone, alfentanil, buprenorphine, butorphanol, fentanyl, sufentanyl, meperidine, methadone, nabulfina, propoxyphene, pentazocine and their pharmaceutically acceptable salt derivatives.

16. The method according to claim 15, wherein the opioid analgesic is morphine or a pharmaceutically acceptable salt thereof.

17. The method according to claim 16, wherein the opioid analgesic is fentanyl or a pharmaceutically acceptable salt thereof.

18. The method according to claim 11, wherein the pain is chronic pain.

19. The method according to claim 11, wherein the pain is acute pain.

20. The method according to claim 11, wherein the pain is caused by pancreatitis, kidney stones, headaches, dysmenorrhoea, musculoskeletal pain, sprains, visceral pain, ovarian cysts, prostatitis, cystitis, interstitial cystitis, inflammatory bowel disease, post-operative pain (including dental pain), post-surgical pain, migraine, trigeminal neuralgia, pain from burns and/or wounds, pain associated with trauma (including traumatic head injury), neuropathic pain, post-herpetic neuralgia, pain associated with musculoskeletal diseases, rheumatoid arthritis, osteoarthritis, ankylosing spondilitis, periarticular pathologies, oncological pain (including "breakthrough pain" and pain associated with terminal cancer), pain from bone metastases, or pain from HIV.

21. The method according to claim 11, wherein the amount of anti-TrkA antibody is such that the opioid dose is reduced by at least 5% of that necessary to produce the same analgesic effect by itself.

* * * * *

UNITED STATES PATENT AND TRADEMARK OFFICE
CERTIFICATE OF CORRECTION

PATENT NO. : 7,988,966 B2
APPLICATION NO. : 11/921266
DATED : August 2, 2011
INVENTOR(S) : Flaminia Pavone et al.

It is certified that error appears in the above-identified patent and that said Letters Patent is hereby corrected as shown below:

In the Claims:

At column 27, claim number 4, line number 1, ~~hydomorphone~~ hydromorphone

At column 27, claim number 4, line number 3, ~~nabulfina~~ nalbuphine

At column 27, claim number 8, line number 24, ~~hydomorphone~~ hydromorphone

At column 27, claim number 8, line number 26, ~~nabulfina~~ nalbuphine

At column 28, claim number 15, line number 12, ~~hydomorphone~~ hydromorphone

At column 28, claim number 15, line number 14, ~~nabulfina~~ nalbuphine

Signed and Sealed this
Eighth Day of November, 2011

David J. Kappos
*Director of the United States Patent and Trademark Office*